United States Patent
Wirth et al.

(10) Patent No.: US 10,722,198 B2
(45) Date of Patent: Jul. 28, 2020

(54) PORTABLE RADIOLOGICAL CASSETTE COMPRISING PATIENT IDENTIFICATION MEANS

(71) Applicant: TRIXELL, Moirans (FR)

(72) Inventors: Thibaut Wirth, Moirans (FR); Beatriz Matesanz Garcia, Velizy Villacoublay (FR); Jacky Dutin, Moirans (FR)

(73) Assignee: TRIXELL, Moirans (FR)

( * ) Notice: Subject to any disclaimer, the term of this patent is extended or adjusted under 35 U.S.C. 154(b) by 59 days.

(21) Appl. No.: 15/738,534

(22) PCT Filed: Jun. 21, 2016

(86) PCT No.: PCT/EP2016/064243
§ 371 (c)(1),
(2) Date: Dec. 20, 2017

(87) PCT Pub. No.: WO2017/005482
PCT Pub. Date: Jan. 12, 2017

(65) Prior Publication Data
US 2018/0184996 A1  Jul. 5, 2018

(30) Foreign Application Priority Data
Jul. 8, 2015  (FR) ..................... 15 01445

(51) Int. Cl.
*A61B 6/00* (2006.01)
*G16H 10/65* (2018.01)
*G06K 7/14* (2006.01)

(52) U.S. Cl.
CPC .......... *A61B 6/4494* (2013.01); *A61B 6/4283* (2013.01); *A61B 6/4405* (2013.01);
(Continued)

(58) Field of Classification Search
CPC ............... A61B 6/4283; A61B 6/4494; G06K 19/06037; G16H 10/65; G03B 42/04; G03B 42/047; G03B 42/08; G03B 2206/006
See application file for complete search history.

(56) References Cited

U.S. PATENT DOCUMENTS 5,264,684 A * 11/1993 Weil .................. B82Y 15/00
                                          235/375
5,757,021 A    5/1998 Dewaele
(Continued)

FOREIGN PATENT DOCUMENTS

JP    2006-25830 A    2/2006
JP    2008-188330 A   8/2008
(Continued)

*Primary Examiner* — Suezu Ellis
(74) *Attorney, Agent, or Firm* — Baker & Hostetler LLP

(57) ABSTRACT

A portable radiological cassette comprises a housing, and a digital detector of incident ionizing radiation, taking the form of a flat panel, the detector being positioned in the housing and comprising a memory space, and being intended to generate a digital image of a patient exposed to the ionizing radiation and with whom an identification code is associated, the digital image being stored in the memory space. The cassette comprises a device for selecting the identification code of the patient, which is intended to write the identification code of the patient in the memory space. The invention also relates to a method for identifying a patient.

7 Claims, 5 Drawing Sheets

(52) U.S. Cl.
CPC ......... *G06K 7/1413* (2013.01); *G06K 7/1417* (2013.01); *G16H 10/65* (2018.01); *A61B 2560/0214* (2013.01); *A61B 2560/0475* (2013.01)

(56) References Cited

U.S. PATENT DOCUMENTS

| | | | | |
|---|---|---|---|---|
| 2004/0088193 | A1* | 5/2004 | Moriyama | G06F 19/321 |
| | | | | 705/3 |
| 2004/0190781 | A1* | 9/2004 | Shiibashi | G06Q 10/10 |
| | | | | 382/210 |
| 2005/0051447 | A1* | 3/2005 | Nakajo | G03B 42/04 |
| | | | | 206/455 |
| 2007/0269017 | A1* | 11/2007 | Umeki | A61B 8/4416 |
| | | | | 378/165 |
| 2009/0022276 | A1* | 1/2009 | Ohara | A61B 6/00 |
| | | | | 378/101 |
| 2009/0026392 | A1* | 1/2009 | Yoshimi | A61B 6/4283 |
| | | | | 250/582 |
| 2009/0194695 | A1* | 8/2009 | Nishino | A61B 6/56 |
| | | | | 250/336.1 |
| 2011/0073765 | A1 | 3/2011 | Ohta et al. | |
| 2017/0360390 | A1* | 12/2017 | Tajima | A61B 6/12 |

FOREIGN PATENT DOCUMENTS

| | | |
|---|---|---|
| JP | 2009-50688 A | 3/2009 |
| JP | 2010-131411 A | 6/2010 |
| WO | 2015/076081 A1 | 5/2015 |

\* cited by examiner

PORTABLE RADIOLOGICAL CASSETTE COMPRISING PATIENT IDENTIFICATION MEANS

CROSS-REFERENCE TO RELATED APPLICATIONS

This application is a National Stage of International patent application PCT/EP2016/064243, filed on Jun. 21, 2016, which claims priority to foreign French patent application No. FR 1501445, filed on Jul. 8, 2015, the disclosures of which are incorporated by reference in their entirety.

FIELD OF THE INVENTION

The invention relates to the field of imaging. It may be applied to any type of imager, in particular infrared, visible and x-ray imagers. The invention is described here with respect to the field of medical x-ray imaging, by way of example and without loss of applicability to other imaging fields. The invention relates to a portable radiological cassette with patient-identifying means. The invention also relates to a method for identifying a patient on whom radiography must be performed.

The invention relates to a portable radiological cassette with which a digital radiological system is intended to be equipped. The cassette comprises a digital detector of ionizing radiation allowing an image to be delivered depending on the radiation received.

BACKGROUND

A radiological system comprises a source of ionizing radiation, such as for example an x-ray tube, allowing x-ray radiation to be generated, and a base station comprising an information-processing system allowing the x-ray tube and the detector to be synchronized and also allowing image processing operations to be carried out so as to present the operator with an image that is corrected for any inherent defects in the detector and improved, for example via edge-restoring processing. An object the x-ray image of which it is desired to obtain is placed between the source and the detector. Such a system may be used in many applications such as for example medical radiology and nondestructive testing. The invention may also be implemented with other types of radiation to be detected, in particular gamma radiation.

In the past, radiological systems were bulky and difficult to move. It was necessary to position the object with respect to the system in order to obtain the desired image. With the appearance of solid-state detectors, the detector has become less bulky and it has become possible to move the detector with respect to an object that remains stationary. For medical radiology, digital detectors have been produced in the form of movable cassettes that it is possible to place in immediate proximity to a patient an image of whom it is desired to take, when the state of health of the patient prevents them from moving to a room reserved for radiology.

Movable cassette essentially comprises a digital detector of ionizing radiation taking the form of a flat panel and a circuit board that in particular controls the digital detector. The detector and the board are placed in a housing that protects them mechanically.

In mobile radiography, for example when the radiography is carried out at the bedside of a patient who is unable to move, it is essential for the radiograph obtained to be associated with this patient. Generally therefore, each obtained radiograph must be associated with the right patient.

The radiography may be carried out by means of what are called analog cassettes i.e. cassettes of film/screen type or of photostimulable-phosphor-plate cassettes (also known as PSP cassettes from the abbreviation of photostimulable phosphor plate or as CR cassettes from the abbreviation of computed radiography). Radiographs are achieved with PSP cassettes by virtue of a film integrated into the cassette, which is able to store an image. The film is read subsequently by a separate reader in a workstation. Thus, a cassette allows only a single radiograph to be taken at a time. Operators who want to take a plurality of radiographs of various patients must therefore provide a plurality of cassettes, thereby creating a risk of mix-up of the cassettes and of confusion as to the identification of the patients. It is possible to stick a label with the name or the code of the patient on the back of each cassette, in order to decrease the risk of incorrect attribution of the image to the patient during the development of the radiograph. The labels may be taken from the bedside of the patient or be printed beforehand. This solution is nevertheless not completely satisfactory in a hospital environment. Specifically, radiographs taken at the bedside of patients are generally taken during a ward round. It is necessary to provide a plurality of cassettes, and the risk of confusion as to the identification of the patient remains.

Another solution consists in generating codes (for example barcodes). A cassette receives a barcode. The operator notes on the cassette the name of the patient, and optionally the radiographed part. Using a barcode reader, the code is read out and the image that will be produced is then attributed to the patient chosen by the operator. This solution involves the barcode being read out after the ward round, at the workstation. It therefore requires the operator to open, at the workstation, the record of the right patient before initiating the cassette readout. The risk of confusion between patients and images is still present and it is still necessary to provide a plurality of cassettes if a plurality of radiographs are to be taken, this being burdensome.

As mentioned above, cassettes that are what are called digital cassettes and that are sensitive to x-ray radiation do exist. There is no need for a digital cassette to be connected to the x-ray generator, the cassette detects x-rays by itself and records images as they are taken. In other words, a single digital cassette may contain a plurality of images. This solution has the advantage that the operator no longer needs to take a plurality of cassettes with him when he is required to take a plurality of radiographs. In contrast, once again, the risk of confusion as to the identification of the patient to which each stored image corresponds is real since the digital cassette contains a plurality of images and it is necessary to be able to determine to which patient each of the produced images stored in the cassette corresponds. One possible way of decreasing the risk of confusion as to the identification of the patient is to attribute a barcode to the patient, which barcode is read out, before the radiography, with an additional barcode reader by the operator. This readout allows the record of the patient to be opened on the computer of the mobile radiology apparatus. However, such a solution therefore requires a mobile radiology system comprising a cassette reader and a computer to acquire the image. This solution is not stand-alone since it is necessary to provide a trolley with a computer and cassette reader. In addition, this solution is not compatible with adaptation to pre-existing structures for cassettes designed to hold silver-based films of dimensions defined by standard ISO4090.

One solution consists in integrating a small screen into the digital cassette. This small screen allows a number that is incremented each time an image is taken to be displayed. This number therefore corresponds to the number of images stored in memory in the detector. Radiograph number 1 belongs to the first patient, radiograph number 2 belongs to the second patient, etc. Or indeed, if the operator is required to take a plurality of radiographs of the same patient, radiograph number 1 may belong to a first patient, radiograph number 2 may belong to patient number 2, and radiograph number 3 may belong to the same patient number 2. Moreover, in addition to identifying the patient, it is necessary to identify what part of the body was radiographed. The risk of mix-up between stored images and patients is high during the download of the images to the workstation. Specifically, it is up to the operator to manually note, for example on the chart of the patient or in his own clinical notes, the number displayed on the small screen of the cassette when he takes a radiograph of a patient, and optionally the radiographed part of the body. If the operator wants to avoid this source of error due to manual notation of the displayed number on the chart of the patient, it is possible to attribute beforehand codes to the patients. But this solution then obliges the operator to respect, when taking the radiographs, the numerical order thus established. In other words, if the displayed number is considered to be an identification code of the patient (the number 1 being defined beforehand as being attributed to such a patient, the number 2 being attributed to another such patient, etc.), the order in which the radiographs must be taken is set beforehand and if not respected may lead to stored images and patients being incorrectly associated during the download of the images to the workstation.

SUMMARY OF THE INVENTION

The invention aims to remove any risk of confusion between the radiographs of patients, while enabling a mode of use of the digital cassette that is completely stand-alone, i.e. that requires no additional portable reader, nor radiographs to be taken in a preset order.

To this end one subject of the invention is a portable radiological cassette comprising:

a housing; and a digital detector of incident ionizing radiation, taking the form of a flat panel, the detector being positioned in the housing and comprising a memory space, and being intended to generate a digital image of a patient exposed to the ionizing radiation and with whom an identification code is associated, the digital image being stored in the memory space;

characterized in that it comprises a device for selecting the identification code of the patient, which is intended to write the identification code of the patient in the memory space.

Advantageously, the digital image is stored in the memory space and the identification code of the patient is written in the memory space.

According to one embodiment, the identification code of the patient is a barcode, and the device for selecting the identification code of the patient is a barcode reader.

According to another embodiment, the identification code of the patient is a QR code and the device for selecting the identification code of the patient is a QR-code reader.

According to another embodiment, the memory space comprises a first zone and a second zone, and the digital image is stored in the first zone of the memory space and the device for selecting the identification code of the patient is a human-machine interface configured so that a user can choose the identification code from a list of patients that is available in the second zone of the memory space of the detector.

According to another embodiment, the human-machine interface comprises a touchscreen allowing a patient to be selected from a list of patients that is available in the second zone of the memory space of the detector.

According to another embodiment, the human-machine interface comprises a screen and at least one button, the screen allowing a list of patients that is available in the second zone of the memory space of the detector to be displayed and the at least one button allowing a patient to be selected from the list.

Advantageously, the portable radiological cassette comprises means for consulting a list of patients on a remote server.

Advantageously, the portable radiological cassette furthermore comprises a display screen intended to display the identification code read.

The invention also relates to a method for identifying a patient exposed to ionizing radiation with whom an identification code is associated, implementing such a portable radiological cassette, and comprising:

a step of selecting the identification code of the patient with the device for selecting the identification code; and a step of writing the identification code of the patient in the memory space of the detector of the cassette.

BRIEF DESCRIPTION OF THE DRAWINGS

The invention will be better understood and other advantages will become apparent on reading the detailed description of one embodiment that is given by way of example, the description being illustrated by the appended drawing, in which.

DETAILED DESCRIPTION

For the sake of clarity, the drawings are not to scale. In addition, elements that are the same have been given the same references in the various figures. The invention is described with respect to the field of medical imaging with x-rays but it is applicable to imaging with any other type of ionizing radiation, gamma rays for example.

Figure 1:
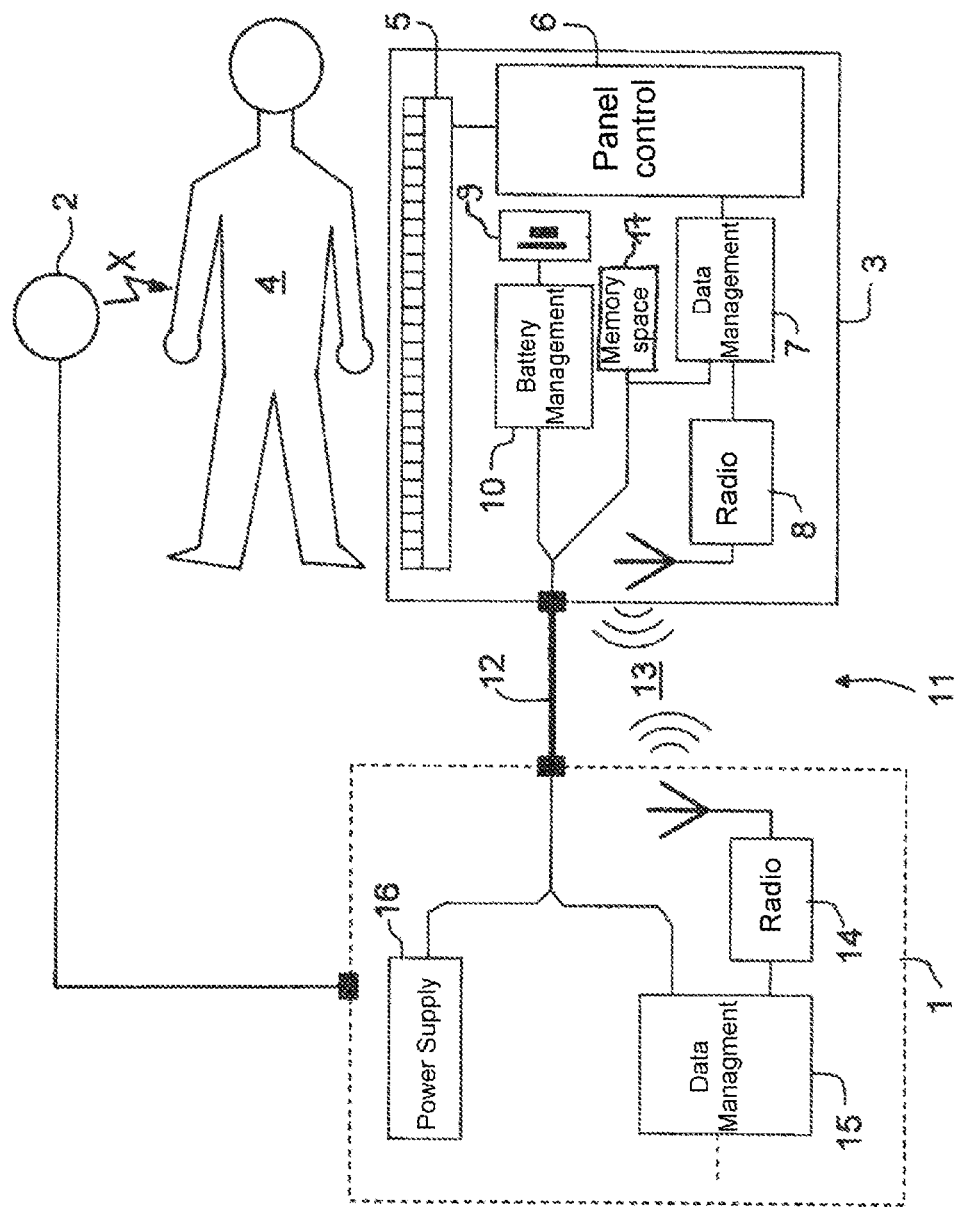
FIG. 1 schematically shows an example of a radiological system implementing the invention.

FIG. 1 schematically shows an example of a radiological system implementing the invention. FIG. 1 shows a radiological system intended for medical use. The system includes a stationary base station 1, an x-ray generator 2 and a radiation detector taking the form of a portable cassette 3. The cassette allows an image of a patient 4 through whom the x-ray radiation generated by the radiation generator 2 has passed to be obtained. The cassette 3 includes a digital detector produced in the form of a flat panel 5, which is connected to a control module 6 allowing the image obtained by the flat panel 5 to be read and said image to be digitized by way of an analog-to-digital converter. The movable cassette 3 also includes a data-management module 7, a radio module 8, a battery 9 and a battery-management module 10. The movable cassette comprises a memory space 17 that is intended to store the digitized image.

The base station includes a radio module 14, a data-management module 15 and a power supply 16.

Means 11 for communicating between the cassette 3 and the base station 1 allow data such as the image to be transferred between the cassette 3 and the base station 1. Data may be passed either from the base station 1 to the cassette 3, or from the cassette 3 to the base station 1. To the cassette 3, it is for example a question of data allowing the flat panel 5 to be controlled, and to the base station 1 of data for example including images taken by the flat panel 5.

The communicating means may comprise a disconnectable wired link 12 and/or a wireless link 13. The two links 12 and 13 are both capable of transferring data. The two radio modules 8 and 14 allow data to be exchanged between the base station 1 and the cassette 3. The data-management module 7 of the cassette 3 allows data received or originating from the control module 6 to be routed to one of the links 12 or 13. Likewise, in the base station 1, the data-management module 15 allows data received or originating from one of the links 12 or 13 to be routed. The power supply 16 delivers the electrical power required for operation of the various modules of the base station 1 and the cassette 3.

The cassette 3 is supplied with power via the wired link 12 or the battery 9. Advantageously, the system includes means for recharging the battery 9. More precisely, the management module of the battery 10 measures the charge of the battery 9 and has it recharged where needs be.

Figure 2:
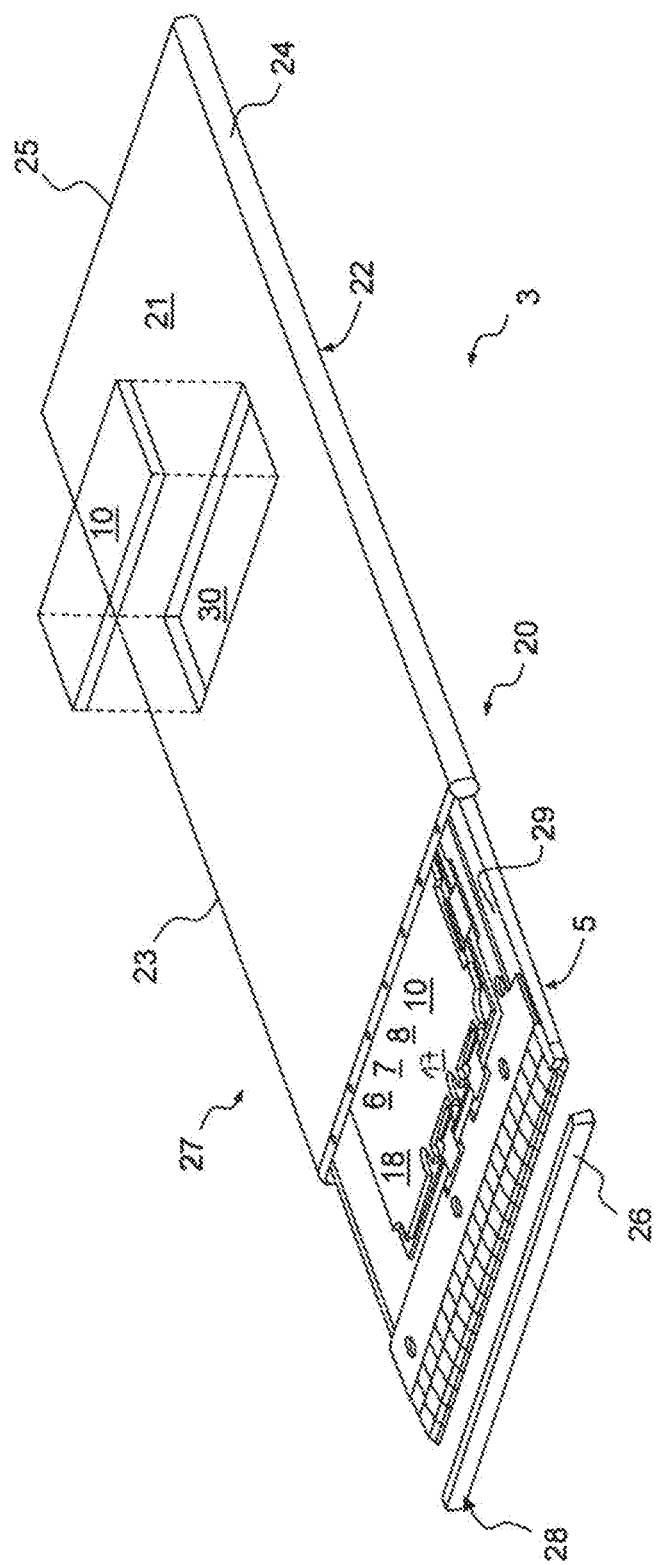
FIG. 2 shows an exploded view of an example of a portable cassette.

FIG. 2 shows an exploded view of an example of a portable cassette. The cassette comprises a housing 20 having an essentially parallelepipedal shape, in which housing the digital detector 5 and a circuit board 18 that manages the detector 5 are placed. With reference to FIG. 1, the circuit board 18 for example comprises the control module 6, the data-management module 7, the radio module 8, and the management module of the battery 10. These four modules are given merely by way of example. They are not obligatory for the implementation of the invention. The battery 9 is placed on the exterior of the housing 20 in order to make its eventual replacement easier. The circuit board 18 also comprises the memory space 17.

The housing 20 possesses six main faces 21 to 26 defining the parallelepipedal shape. The six faces are parallel pairwise. The detector 5, which takes the form of a flat panel, possesses a radiation-detecting area that is close to that of the two largest faces 21 and 22. The parallel faces 25 and 26 are the two smallest faces of the housing 20.

The housing 20 for example comprises a jacket 27 formed of a unitary mechanical part forming the five faces 21 to 25 of the essentially parallelepipedal shape, including the two largest faces 21 and 22. The housing 20 may furthermore comprise a cap 28 allowing face 26 of the essentially parallelepipedal shape to be plugged. Alternatively, the cap 28 may plug face 23 or face 24.

The fact that the housing is a unitary five-faced part allows its rigidity to be greatly increased. More particularly, the three smallest faces 23, 24 and 25 (26, 23, 25 or 26, 24, 25, respectively, depending on the face plugged by the cap 28) encircle the housing 20 in two perpendicular directions, this increasing the torsional rigidity of the housing 20 around axes parallel to the two largest faces 21 and 22.

The various elements placed in the interior of the housing 20 are securely fastened to one another and are slid into the jacket 27 via the face 26 (23 or 24, respectively, depending on the face plugged by the cap 28) in a translational movement perpendicularly to this face.

It is also possible for the jacket 27 to be a unitary mechanical part forming the four faces 21 to 24. In this case, the housing 20 comprises two caps 28 and 28' allowing the faces 26 and 25 to be plugged. The cap 28 may be what is called a movable cap, and the cap 28' may be what is called a fixed cap. The caps may bear certain functionalities such as connectors. Moreover, the invention is described in the configuration in which the caps 28 and 28' plug the faces 26 and 25. It is of course obvious that the invention may be applied in other configurations in which the caps 28 and 28' plug two faces among the faces 23, 24, 25, 26. More generally, the invention may be applied with a single cap 28 plugging one of these faces.

The battery 10 is housed in the interior of the parallelepipedal volume formed by the housing 20. The battery 10 is housed from the exterior of the cassette 3 in a recess 30 in the face 21. Face 22, i.e. the face opposite face 21, is intended to be passed through by the ionizing radiation to be detected. The digital detector 5 is placed in the interior of the housing 20 on the side of face 22.

In the past, medical radiology used silver-based films that were handled in cassettes. Standard ISO 4090 defined the dimensions of the cassettes designed to hold such silver-based films. The thickness of such conventional cassettes, as defined by the standard, is comprised between 13 and 16 mm. Advantageously, the cassette meets, as regards its dimensions, the requirements of standard ISO 4090. More particularly, the overall thickness of the cassette 3 measured between the two largest faces 21 and 22 is smaller than 16 mm. This allows means used to store such conventional cassettes to be used to store a digital cassette 3.

As explained above, a single digital cassette may contain a plurality of images. This solution has the advantage that the operator no longer needs to take a plurality of cassettes with him when he is required to take a plurality of radiographs, for example during a ward round for taking one or more radiographs of a plurality of patients. Nevertheless, the fact that a digital cassette can contain a plurality of images leads to a risk of confusion as to the identification of the patient to which each stored image corresponds. Specifically, since the digital cassette contains a plurality of images, it is necessary to be able to determine to which patient each of the produced images stored in the cassette corresponds.

Figure 3:
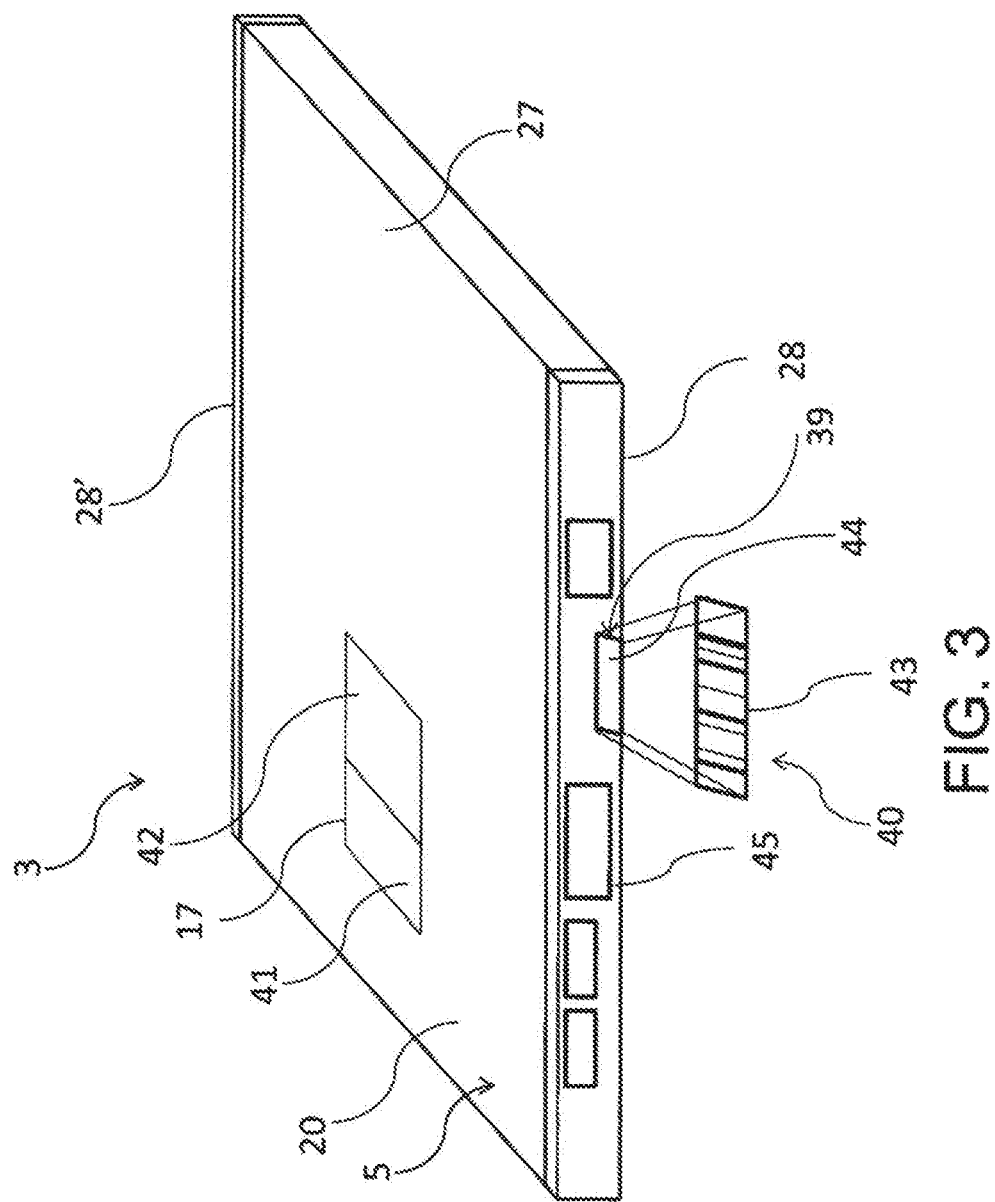
FIG. 3 schematically shows a first embodiment of a cassette according to the invention.

FIG. 3 schematically shows a first embodiment of a cassette according to the invention. The cassette 3 is identical to the cassette presented in FIG. 2 and may be implemented in the same way as the cassette presented in FIG. 1. The portable radiological cassette 3 comprises a housing 20, a digital detector of incident ionizing radiation taking the form of a flat panel, the detector 5 being positioned in the housing 20 and comprising a memory space 17, and being intended to generate a digital image of a patient exposed to the ionizing radiation and with whom an identification code 40 is associated, the digital image being stored in the memory space 17. According to the invention, the cassette 3 comprises a device 39 for selecting the identification code 40 of the patient, which is intended to write the identification code 40 of the patient in the memory space 17. Thus, each image stored in the memory space 17 is associated with an identification code 40 of the patient. The invention allows the operator to be able to take radiographs of patients in any order, this order not needing to be defined beforehand since at the moment at which the image of a patient is taken, the identification code 40 of the patient is also recorded in the memory space 17 of the cassette 3. Recording the identification code 40 of the patient in the memory space 17 allows any risk of confusion between the radiographs of patients to be avoided. In addition, a preset radiograph order is not necessary, this freeing the operator from this constraint during his ward round. As the cassette 3 comprises the selecting device 39, the operating mode of the digital cassette is completely stand-alone, i.e. no additional portable reader is required, thereby allowing the bulk of the mobile radiography apparatus to be decreased. In addition, the cassette 3 is compatible with adaptation to pre-existing structures for cassettes designed to hold silver-based films of dimensions defined by standard ISO4090.

In other words, the detector may generate a plurality of digital images of patients exposed to ionizing radiation. An identification code is associated with each of the patients, and each image of the plurality of digital images of a patient is stored in the memory space. Moreover, the device for selecting the identification code of the patient may write the identification code of the patient in the memory space. In other words, the invention allows images to be generated, for example three images denoted I1, I2, I3. The images I1, I2, I3 are stored in the memory space of the cassette. A code corresponds to each of these images, for example C1 for the image I1, C2 for the image I2, C3 for the image I3. If the code corresponds to the name of a patient and the images I1 and I2 are of the same patient, then the images I1 and I2 may both have the same code, P1 for example, and the image I3 of another patient may have the code P2. The memory space of the cassette is therefore a zone in which it is possible to save a piece of information associated with a least one of the generated images, the piece of information possibly being an identification code, a name of a patient, a social security number of a patient and/or a radiographed body part. Of course, the memory space may contain a combination of pieces of information.

More precisely, the memory space 17 may be divided into two portions and comprise a first zone 41 and a second zone 42. The digital image is stored in the first zone 41 of the memory space 17 and the identification code 40 of the patient may be written in the first zone 41 of the memory space. This partition of the memory space 17 may allow the identification code 40 of the patient to be written on the digital image. In other words, the identification code 40 of the patient may be directly integrated into the header of the image stored in the memory of the detector 5.

In FIG. 3, the casing 27 is formed of a unitary mechanical part forming four faces. Furthermore, the housing 20 comprises two caps 28 and 28' allowing faces to be plugged. In this first embodiment, the cap 28 is a movable cap and the cap 28' is a fixed cap.

The identification code 40 of the patient may be a code and the device 39 for selecting the patient a code reader. In particular, the identification code 40 of the patient may be a barcode 43 and the device 39 for selecting the patient a barcode reader 44. Likewise, the identification code 40 of the patient may be a QR code (QR being the abbreviation of the expression "quick response" meaning that the content of the code may be decoded rapidly after having been read) and the device 39 for selecting the patient a QR-code reader. QR code has the advantage of being able to store more information than a barcode. Generally, the invention may be applied with any other type of code able to be read by a reader associated with this type of code. The invention also applies to a selecting device 39 such as an optical reader (of the video-camera type) able to read any type of information (barcode, QR code and any other symbol or letter).

In FIG. 3, the barcode reader 44 is positioned on the mobile cap 28. The cassette 3 according to the invention may also comprise a display screen 45 intended to display the identification code 40 read. This display screen 45 in particular allows the operator to make an additional check of the identification of the patient. The positions of the elements in FIG. 3 are given by way of example. It will be understood that the invention is not limited to these positions. For example, the display screen 45 may also be positioned on the fixed cap 28' or even on the back face of the cassette 3.

Figure 4:
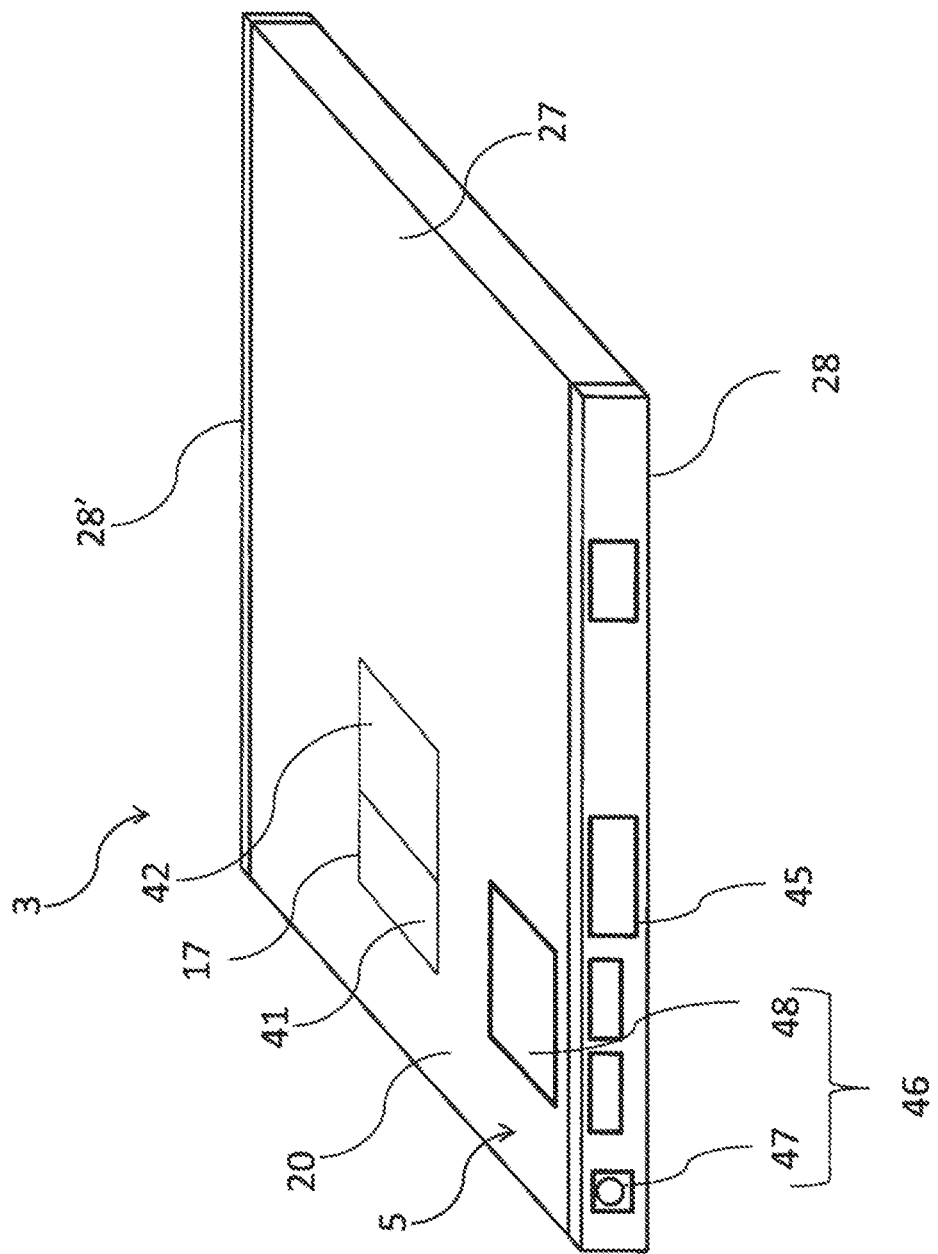
FIG. 4 schematically shows a second embodiment of a cassette according to the invention.

FIG. 4 schematically shows a second embodiment of a cassette according to the invention. The cassette 3 shown in FIG. 4 is identical to the cassette shown in FIG. 3 except as regards the device 39 for selecting the identification code 40 of the patient. In FIG. 4, the device 39 for selecting the identification code 40 of the patient is a human-machine interface 46, also known by its abbreviation HMI, this interface being configured so that a user can choose the identification code 40 from a list of patients that is available in the second zone 42 of the memory space 17 of the detector 5.

The human-machine interface 46 may comprise a screen 48 and at least one button 47, the screen 48 allowing a list of patients that is available in the second zone 42 of the memory space 17 to be displayed and the button 47 allowing a patient to be selected from the list. More exactly, the screen 48 allows a list of patients that is available in the second zone 42 of the memory space 17 or a list of identification codes 40 that is also available in the second zone 42 of the memory space 17, to be displayed.

Alternatively, the screen 48 may be a multi-touchscreen allowing various displays to be displayed at will, in particular a preview of the radiograph or any other display of information that the operator may desire.

Alternatively, the screen 48 may be a touch screen allowing a patient to be selected directly (no additional button required) from a list of patients that is available in the second zone 42 of the memory space 17 of the detector. Likewise, the screen 48 allows a list of patients that is available in the second zone 42 of the memory space 17 or a list of identification codes 40 of patients that is also available in the second zone 42 of the memory space 17, to be displayed. In this second embodiment, the available list of patients and/or their identification code 40 in the second zone 42 of the memory space 17 of the detector will have been downloaded beforehand.

For example, before starting his ward round, the operator downloads into the cassette 3 the list of all the patients of whom it is desired to take a radiograph. During his round, the operator may thus choose the order in which he will radiograph the patients. Advantageously this means that the order in which the radiographs need to be taken is not set by a list made beforehand. Thus, if a patient is unavailable (for example because he is asleep or receiving care), the operator may take the radiograph latter on, at the end of his round for example, without however generating confusion in the digital images since each image will be attributed to the right patient i.e. the patient to which the image corresponds.

Advantageously, the cassette 3 according to the invention may comprise means for consulting a list of patients on a remote server. For example, in a hospital environment in which a data server that is accessible by wireless connection is available, the means for consulting the list of patients may be communicating means comprising the wireless link 13, the data-management module 7 and the radio module 8. The list of patients may thus be recorded in the data server of the hospital environment. The advantage of this configuration is to allow the operator not to have to do download prior to his ward round the list of patients of whom he desires to take a radiograph. By virtue of the wireless connection, the operator has access, via the human-machine interface 46, to the list of patients on the data server. After the patient has been chosen, the operator may take the radiograph. The identification code 40 of the patient may then be integrated into the header of the image stored in the memory of the detector. Next, the operator may take other radiographs of other patients. During the download of images stored in a server of the medical environment, each of the images may be automatically assigned to the respective record of the patients.

As already mentioned in the description, the main advantage of the invention is to allow the digital cassette to be used in a completely stand-alone mode, without risk of confusion between the radiographs of patients, and without the need for an additional portable reader or for radiographs to be taken in a preset order.

Figure 5:
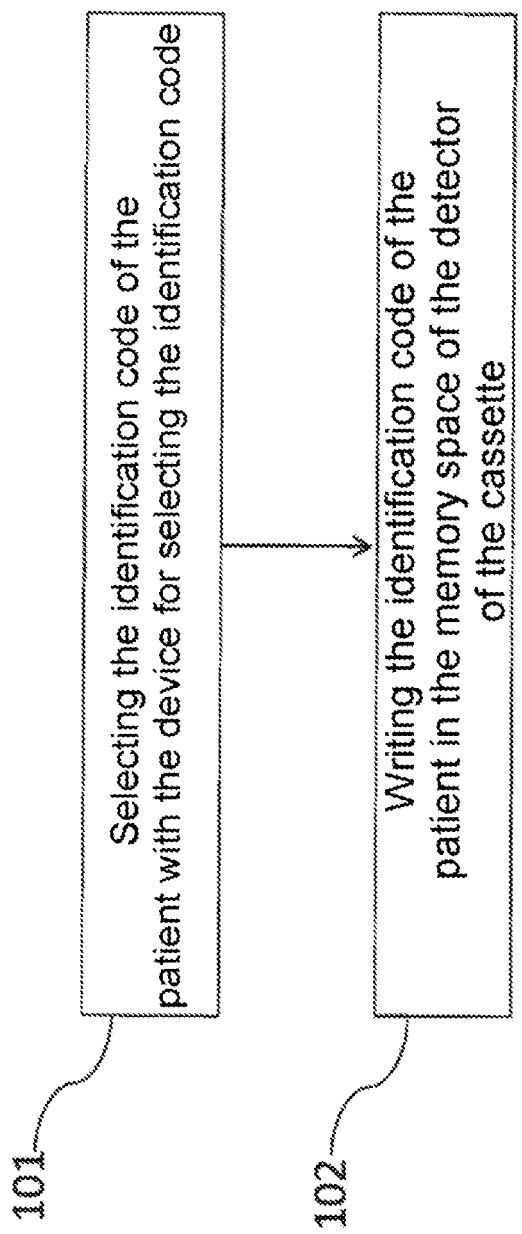
FIG. 5 shows the steps of a method for identifying a patient according to the invention.

FIG. 5 shows the steps of a method for identifying a patient of which a radiograph must be taken. According to the invention, the method for identifying the patient comprises a step 101 of selecting the identification code 40 of the patient with the device 39 for selecting the identification code 40, and a step 102 of writing the identification code 40 of the patient in the memory space 17 of the detector 5 of the cassette 3.

The invention has been described with respect to a case of application to radiography in a medical environment. It is clearly obvious that the invention may also be applied in other fields and/or with other types of ionizing radiation.

The invention claimed is:

1. A portable radiological cassette, comprising:
   a housing;
   code reader; and
   a digital detector of incident ionizing radiation, taking the form of a flat panel, the detector (i) being positioned in the housing, (ii) comprising a single memory space, and (iii) being configured to generate a plurality of digital images of patients exposed to the ionizing radiation, wherein an identification code is associated with each of the patients, each image of the plurality of digital images of a patient being stored in the single memory space;
   wherein the identification code of the patients is selected via the code reader, and
   wherein the identification code of the patients is written in the single memory space to associate in the single memory space each image of the plurality of digital images to a patient.

2. The portable radiological cassette as claimed in claim 1, wherein the plurality of digital images is stored in the single memory space.

3. The portable radiological cassette as claimed in claim 1,
   wherein the code reader is a barcode reader,
   wherein the identification code of the patients is a barcode.

4. The portable radiological cassette as claimed in claim 1,
   wherein the code reader is a quick response (QR)-code reader,
   wherein the identification code of the patients is a QR code.

5. The portable radiological cassette as claimed in claim 1, further comprising a display screen intended to display the identification code.

6. The portable radiological cassette as claimed in claim 1, wherein an operating mode of the portable radiological cassette is completely stand-alone.

7. A method for identifying a patient exposed to ionizing radiation with whom an identification code is associated, implementing a portable radiological cassette as claimed in claim 1, comprising:
   a step of selecting the identification code of the patient; and
   a step of writing the identification code of the patient in the single memory space of the detector of the cassette.

\* \* \* \* \*